(12) United States Patent
Burrell et al.

(10) Patent No.: US 7,454,248 B2
(45) Date of Patent: *Nov. 18, 2008

(54) METHOD, APPARATUS AND PRODUCT FOR ACQUIRING CARDIAC IMAGES

(75) Inventors: Marc Anthony Burrell, Glendale, WI (US); Jasbir S. Sra, W. 305 N. 2963 Red Oak Ct., Pewaukee, WI (US) 53072

(73) Assignees: GE Medical Systems Global Technology, LLC, Waukesha, WI (US); Jasbir S. Sra, Pewaukee, WI (US)

( * ) Notice: Subject to any disclaimer, the term of this patent is extended or adjusted under 35 U.S.C. 154(b) by 605 days.

This patent is subject to a terminal disclaimer.

(21) Appl. No.: 10/707,993

(22) Filed: Jan. 30, 2004

(65) Prior Publication Data

US 2005/0187587 A1 Aug. 25, 2005

(51) Int. Cl.
*A61N 1/00* (2006.01)
*A61B 6/00* (2006.01)
*A61B 5/04* (2006.01)

(52) U.S. Cl. .................. 607/9; 600/428; 600/509

(58) Field of Classification Search ............ 607/9; 600/427–428, 509
See application file for complete search history.

(56) References Cited

U.S. PATENT DOCUMENTS

| | | | |
|---|---|---|---|
| 3,954,098 A | 5/1976 | Dick et al. ............ 128/2.05 Z |
| 4,364,397 A | 12/1982 | Citron et al. |
| 4,547,892 A * | 10/1985 | Richey et al. ................ 378/8 |
| 4,574,807 A | 3/1986 | Hewson et al. ........ 128/419 PG |
| 4,958,632 A * | 9/1990 | Duggan ..................... 607/11 |
| 5,245,287 A | 9/1993 | Nowak et al. ............... 324/322 |
| 5,274,551 A | 12/1993 | Corby, Jr. .............. 364/413.13 |
| 5,304,212 A | 4/1994 | Czeisler et al. ............... 607/88 |
| 5,348,020 A | 9/1994 | Huston ...................... 128/696 |
| 5,353,795 A | 10/1994 | Souza et al. ............. 128/653.2 |
| 5,391,199 A | 2/1995 | Ben-Haim .................. 607/122 |
| 5,431,688 A | 7/1995 | Freeman ..................... 607/10 |
| 5,515,849 A | 5/1996 | Murashita et al. |
| 5,568,384 A | 10/1996 | Robb et al. ............. 364/419.13 |
| 5,738,096 A | 4/1998 | Ben-Haim ............... 128/653.1 |
| 5,765,561 A | 6/1998 | Chen et al. |
| 5,823,958 A | 10/1998 | Truppe ...................... 600/426 |

(Continued)

FOREIGN PATENT DOCUMENTS

EP 1182619 A2 2/2002

(Continued)

OTHER PUBLICATIONS

PCT Search Report for PCT/US2004/020909.

(Continued)

*Primary Examiner*—Mark W Bockelman
(74) *Attorney, Agent, or Firm*—Cantor Colburn LLP

(57) ABSTRACT

A method for acquiring cardiac information from a patient having a pacer for pacing a heart rhythm, an abnormal EKG, or an abnormal heartbeat is disclosed. The method includes: placing a signal injection device proximate the pacer of the patient and injecting a signal across a skin barrier of the patient toward the pacer; in response to the signal received at the pacer, pacing the patient's heart in a fixed asynchronous pacing mode; and, acquiring cardiac information relating to the patient's fixed asynchronously paced heart.

7 Claims, 5 Drawing Sheets

U.S. PATENT DOCUMENTS

| | | | | |
|---|---|---|---|---|
| 5,839,440 | A | 11/1998 | Liou et al. | 128/654 |
| 5,951,475 | A | 9/1999 | Gueziec et al. | 600/425 |
| 6,058,218 | A | 5/2000 | Cline | |
| 6,081,577 | A | 6/2000 | Webber | 378/23 |
| 6,154,516 | A | 11/2000 | Heuscher et al. | 378/15 |
| 6,208,347 | B1 | 3/2001 | Migdal | 345/419 |
| 6,233,304 | B1 | 5/2001 | Hu et al. | 378/8 |
| 6,235,038 | B1 | 5/2001 | Hunter et al. | 606/130 |
| 6,246,898 | B1 | 6/2001 | Vesely et al. | |
| 6,249,693 | B1 | 6/2001 | Cline et al. | 600/410 |
| 6,252,924 | B1 | 6/2001 | Davantes et al. | 378/8 |
| 6,256,368 | B1 | 7/2001 | Hsieh et al. | 378/8 |
| 6,266,553 | B1 | 7/2001 | Fluhrer et al. | 600/428 |
| 6,289,115 | B1 | 9/2001 | Takeo | 382/130 |
| 6,289,239 | B1 | 9/2001 | Panescu et al. | 600/523 |
| 6,314,310 | B1 | 11/2001 | Ben-Haim et al. | 600/424 |
| 6,325,797 | B1 | 12/2001 | Stewart et al. | 606/41 |
| 6,348,793 | B1 | 2/2002 | Balloni et al. | 324/309 |
| 6,353,445 | B1 | 3/2002 | Babula et al. | 345/733 |
| 6,381,485 | B1 | 4/2002 | Hunter et al. | 600/407 |
| 6,389,104 | B1 | 5/2002 | Bani-Hashemi et al. | 378/98.12 |
| 6,411,848 | B2 | 6/2002 | Kramer et al. | 607/9 |
| 6,421,412 | B1 | 7/2002 | Hsieh et al. | 378/9 |
| 6,456,867 | B2 | 9/2002 | Reisfeld | 600/407 |
| 6,468,265 | B1 | 10/2002 | Evans et al. | 606/1 |
| 6,490,475 | B1 | 12/2002 | Seeley et al. | 600/426 |
| 6,490,479 | B2 | 12/2002 | Bock | 600/518 |
| 6,504,894 | B2 | 1/2003 | Pan | 378/8 |
| 6,549,606 | B1 | 4/2003 | Vaillant et al. | 378/4 |
| 6,556,695 | B1 | 4/2003 | Packer et al. | 382/128 |
| 6,584,343 | B1 | 6/2003 | Ransbury et al. | 600/509 |
| 6,650,927 | B1 | 11/2003 | Keidar | 600/424 |
| 6,704,600 | B2 * | 3/2004 | Daum | 607/30 |
| 6,950,689 | B1 | 9/2005 | Willis et al. | |
| 7,047,060 | B1 | 5/2006 | Wu | |
| 7,308,299 | B2 * | 12/2007 | Burrell et al. | 600/428 |
| 2002/0010392 | A1 | 1/2002 | Desai | 600/374 |
| 2002/0046756 | A1 | 4/2002 | Laizzo et al. | 128/899 |
| 2002/0138108 | A1 | 9/2002 | Kralik | 607/9 |
| 2003/0018251 | A1 | 1/2003 | Solomon | 600/427 |
| 2003/0023266 | A1 | 1/2003 | Borillo et al. | 606/200 |
| 2003/0028183 | A1 | 2/2003 | Sanchez et al. | 606/34 |
| 2003/0097219 | A1 | 5/2003 | O'Donnell et al. | 702/19 |
| 2003/0120264 | A1 | 6/2003 | Lattouf | |
| 2003/0187358 | A1 | 10/2003 | Okerlund et al. | 600/443 |
| 2003/0220557 | A1 | 11/2003 | Cleary et al. | 600/409 |
| 2004/0027347 | A1 | 2/2004 | Farsaie | 345/419 |
| 2004/0087850 | A1 | 5/2004 | Okerlund et al. | 600/407 |
| 2004/0225212 | A1 | 11/2004 | Okerlund et al. | 600/407 |
| 2004/0225328 | A1 | 11/2004 | Okerlund et al. | 607/9 |
| 2004/0225331 | A1 | 11/2004 | Okerlund et al. | 607/14 |

FOREIGN PATENT DOCUMENTS

| | | |
|---|---|---|
| EP | 1321101 A2 | 12/2002 |
| WO | WO 91/07726 | 5/1991 |
| WO | WO 96/10949 | 4/1996 |

OTHER PUBLICATIONS

F. H.M. Wittkampf et al.; "Loca Lisa—New Technique for Real-Time 3-Dimensional Localization of Regular Intracardiac Electrodes;" *Circulation*h; 1999; 99: 1312-1317.

"Advanced Vessel Analysis" product descritpion, [online] http://www.gehealthcare.com/usen/ct/clin_app/products/aswessel.html [retrieved Dec. 1, 2004].

"CardIQ" product description, [online], http://egems.gehealthcare.com/geCommunity/Europe/flex_trial/awFlexTrial/aw3_1/eflextrial [retrieved Dec. 1, 2004].

Genevieve Derumeaux et al., Doppler Tissue Imaging Quantitates Regional Wall Motion During Myocardial Ischemia and Reperfusion, Circulation Journal of the American Heart Association, Circulation 1998; 97; 1970-1977.

Olivier Gerard et al., Efficient Model-Based Quantification of Left Ventricular Function in 3-D Echocardiography. IEEE Transactions on Medical Imaging, 21 (9): pp. 1059-1068, Sep. 2002.

Wahle et al., 3D Heart Vessel Reconstruction from Biplane Angiograms, IEEE Computer Graphics and Applications, 16(1): pp. 65-73, Jan. 1996.

Helmut Mair et al., Epicardial Lead Implantation Techniques for Biventricular Pacing via Left Lateral Mini-Thoracotomy, Video Assisted Thoracoscopy and Robotic Approach, The Heart Surgery Forum, 6(5): pp. 412-417, Mar. 2003.

ACC/AHA/ESC Practise Guidelines; Eur. Heart J., vol. 22, issue 20, Oct. 2001; pp. 1854-1923.

M. D. Leash, T. Trepelse, H. Omran, A. Bartorelli, P. Della Bella, T. Nakai, M. Reisman, D. fleschenberb, U. Krumsdorf, and D. Scherer; "Tiny Device Blocks 'Usless' Part of Heart, prevents blood clots;" Journal Report; American Heart Association; Apr. 9, 2002.

Ellen Barlow; "Operating in 3-D" found at www.med.harvard.edu/publications/HMAB/196fo3d.html.

M. Haissaguerre, P. Jais, S. C. Shah, A. Takahashi, M. Hocini, G. Quiniou, S. Garrigue, A. Le Mouroux, P. Le Metayer, and J. Clementy; "Spontaneous Initiation of Atrial Fibrilliation by Ectopic Beats Originating in the Pulmonary Viens;" The New England Journal of Medicine, vol. 339, No. 10, Sep. 3, 1998; pp. 659-668.

C. Pappone, S. Rosanio, G. Augello, G. Gallus, G. Vicedomini, P. Mazzone, S. Gulletta, F. Gugliotta, A. Pappone, V. Santinelli, V. Tortoriello, S. Sala, A. Zangrillo, G. Crescenzi, S. Benussi, and O. Alfieri; "Mortality, Morbidity, and Quality of Life After Circumferential Pulmonary Vien Ablation for Atrial Fibrillation;" Journal of the American College of Cardiology, vol. 42, No. 2; 2003; 185-187.

J. Sra et al., "Current Problems in Cardiology- Atrial Fibrilliation: Epidemiology, Mechanisms, and Management;" Current Problems in Cardiology, Jul. 2000; pp. 406-524.

N. M. Alpert et al., "The Principal Axes Transformation—A Method for Image Registration;" *The Journal of Nuclear Medicine*; 1990; 31:1717-1722.

P. A. van den Elsen et al.; "Medical Image Matching—A Review with Classification;" *IEEE Engineering in Medicine and Biology*, 1993; 26-38.

G. T. Barnes et al.; "Conventional and Spinal Computed Tomography: Physical Principles and Image Quaility Considerations;" *Computed Body Tomography*, 1998, Lippincot-Raven, Philadelphia, PA pp. 1-20.

Milan Sonka and J. Michael Fitzpatrick (eds); *Handbook of Medical Imaging vol. 2. Medical Image Processing and Analysis*; pp. 129-174 & 447-506.

W. M. Feinberg et al.; "Prevalence, Age Distribution, and Gender of Patients with Atrial Fibrillation;" *Arch. Intern. Med. vol. 155*; Mar. 1995; pp. 469-473.

J. L. Cox, J. P. Boineau, R. B. Schuessler, T. B. Ferguson, Jr., M. E. Cain, B. D. Lindsay, P. B. Corr, K. M. Kater, D. G. Lappas; "Operations for Atrial Fibrillation;" Electrophysiology, Pacing and Arrhythmia, Clin. Cardiol. 14, 1991; pp. 827-834.

B.A. Ardekani et al.; "A Fully Automatic Multimodality Image Registration Algorithm;" *Journal of Computer Assisted Tomography*; 1995; 19:615-623.

L. Thurfell et al.; "Registration of Neuroimaging Data: Implementation and Clinical Applications;" *American Society of Neuroimaging*; 2000; 10:39-46.

S. A. Ben-Haim et al.; "Nonfluoroscopic, in vivo navigation and mapping technology;" *Nature Medicine*; 1996, 2:1393-5.

B. Taccardi et al.; "A new intracaitary probe for detecting the site of origin of ectopic ventricular beats during one cardiac cycle;" *Circulation*; 1987; 75:272-81.

F. H.M. Wittkampf et al.; "New Technique for Real-Time 3-Dimensional Localization of Regular Intracardiac Electrodes;" *Circulation*; 1999; 99:1312-17.

V. Fuster et al. "ACC/AHA/NASPE 2002 Guidelines Update for Implantation of Pacemakers and Antiarrhythmia Devices;"J. Am. Coll. Cardiol 2001; 38:1-47.

D. R. Ney "Volumetric Rendering of Computer Tomography Data: Principles and Techniques;" *IEEE Computer Graphics and Applications*; 1990; 24-32.

M. V. Pitzalis et al., "Cardiac Resynchronization Therapy Tailored by Echocardiographic Evaluation of Ventricular Acnchrony;" *J. Am. Coll. Cardiol.* 2002; 40:1615-22.

W. T. Abraham et al., "Cardiac Resynchronization in Chronic Heart Failure;" *N. Engl. J. Med.* 2002; 346:1845-1853.

C. A. Pelizzari et al., "Accurate Three-Dimensional Registration of CT, PET, and/or MR Images of the Brain;" *J. Comput. Assist. Tomogr.* 1989; 13:20-26.

A.C. Evans et al.; "MRI-PET Correlation in Three Dimensions Using a Volume-of-Interest (VOI) Atlas;" *J. Cerb Flow Metab.* 1991; 11:A69-A78.

R.P. Woods et al.; "Rapid Automated Algorithm for Aligning and Reslicing PET Images;" *Journal of Computer Assisted Tomography*, 1992; 16:620-633.

Z. Zhang; "Iterative Point Matching for Registration of Free-Form Curves;" *Inria* 1992, pp. 1-40.

C.L. Grines et al.; "Functional Abnormalities in Isolated Left Bundle Branch Block: The Effect of Interventricular Asynchrony;" *Circulation*; 1989; 79:845-53.

H. B. Xia et al., "Differing effects of right ventricular pacing and left bundle branch block on left ventricular function;" *Br. Heart J.*, 1993; 69:166-173.

S. Cazeau et al., "Effects of Multisite Biventricular Pacing in Patients with Heart Failure and Intraventricular Conduction Delay;" *N. Engl. J. Med.* 2001; 344:873-880.

J. Schreieck et al., "Radiofrequency Ablation of Cardiac Arrhythmias Using a Three-Dimensional Real-Time Position Management and Mapping System;" *Pacing Clin. Ekectrophysiol*, Dec. 2002, 25(12):1699-707.

F. Wittkampf et al., "Real-Time, Three-Dimensional, Nonfluoroscopic Localization of the Lasso Catheter;" *J. Interven. Cardiac Electrophysioll* 2002, 13:630.

J. Sra et al., "Cardiac Chamber Geometry Construction, Catheter Navication and Ablation Using Cutaneous Patches;" *Supplement to Circulation* Oct. 2003, 108 (17): IV-585, Abstract 2667.

J. Sra et al., "Three-Dimensional Right Atrial Geometry Construction and Catheter Tracking Using Cutaneous Patches;" *J. Interven. Cardiac Electrophysiol*, 2003 14:897.

R.J. Schilling et al.; "Simultaneous Endocardial Mapping in the Human Left Ventricle Using a Noncontact Catheter: Comparison of Contact and Reconstructed Electrograms During Sinus Rhythm;" *Circulation* 1998; 98:997-98.

C. C. Gornick et al., "Validation of a New Noncontact Catheter System for Electroanatomic Mapping of Left Ventricular Endocardium;" *Circulation* 1999; 99:829-835.

J. Sra et al., "Noncontact Mapping for Radiofrequency Ablation of Complex Cardiac Arrhythmias;" *J. Interven. Cardiac Electrophysiol* 2001; 5:323-331.

N. M.S. de Groot et al., "Three-Dimensional Catheter Positioning During Radiofrequency Ablation in Patients: First Application of a Real-Time Position Management System;" *J. Interven. Cardiac Electrophysiol* Nov. 2001; 11(11):1183-92.

H. Nikagawa et al., "Role of the Tricuspid Annulus and the Eustachian Valve/Ridge on Atrial Flutter: Relevance to Catheter Ablation of the Septal Isthmus and a New Technique for Rapid Identification of Ablation Success;" *Circulation* 1996; 94:407-24.

L. Gepstein et al., "A Novel Method for Nonfluoroscopic Catheter-Based Electroanatomical Mapping of the Heart: In Vitro and In Vivo Accuracy Results;" *Circulation* 1997; 95:1611-22.

S. Shpun et al., "Guidance of Radiofrequency Endocardial Ablation with Real-time Three-dimensional Magnetic Navigation System;" *Circulation* 1997; 96:2016-21.

J. Sra et al., "Electroanatomic Mapping to Identify Breakthrough Sites in Recurrent Typical Human Flutter;" *Paceing Clin. Electrophysiol* 2000; 23:1479-92.

* cited by examiner

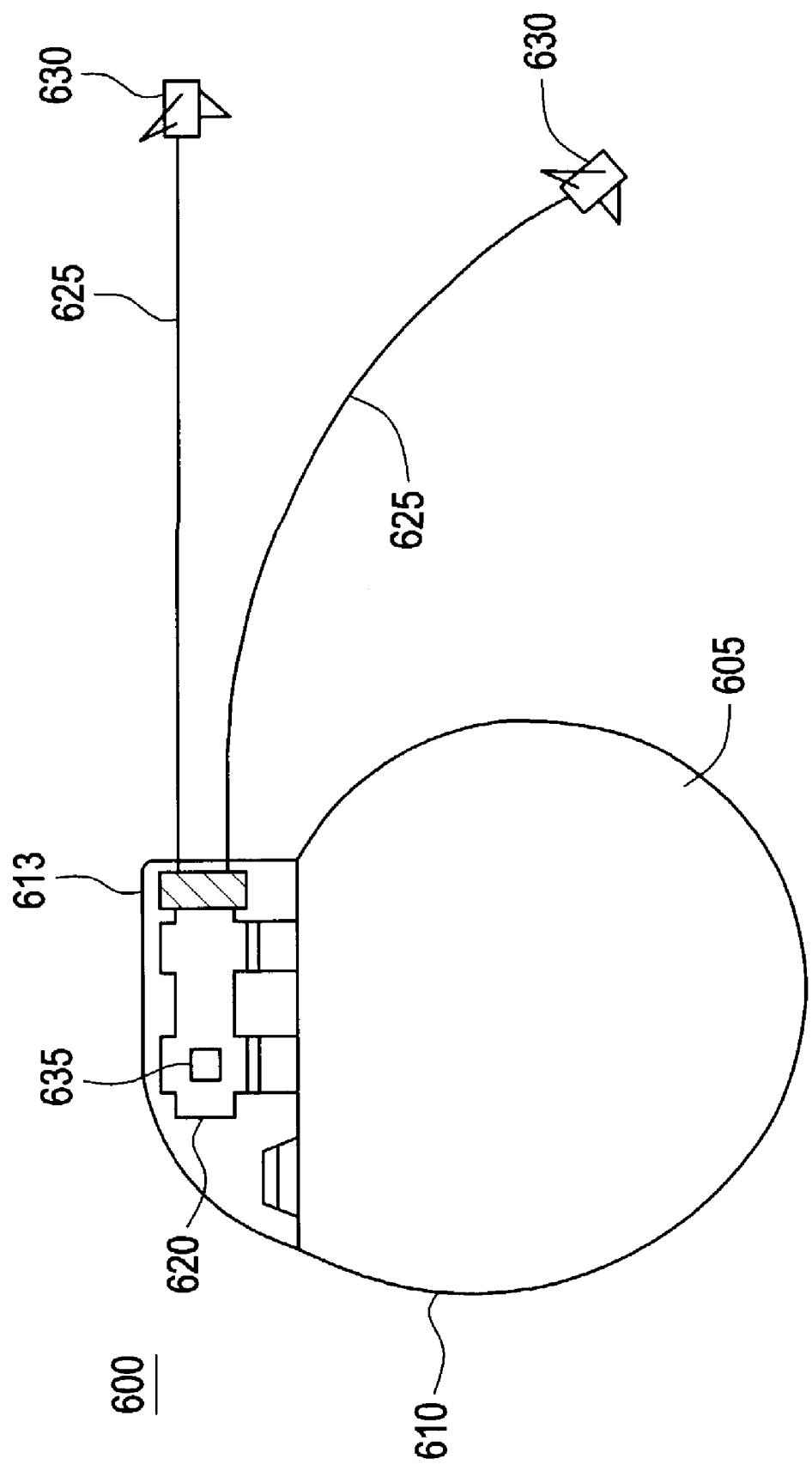

METHOD, APPARATUS AND PRODUCT FOR ACQUIRING CARDIAC IMAGES

BACKGROUND OF INVENTION

The present disclosure relates generally to a method, apparatus, and product, for acquiring a cardiac image from a patient having a paced heart rhythm, or abnormal EKG (such as caused by Left Branch Bundle Block, Atrial fibrillation, or other heart diseases), and particularly to the acquisition of a cardiac image from a patient having a paced heart rhythm by applying a process of magnetic signal injection for improving the quality of the cardiac image.

Patients having cardiac electrical abnormalities, such as from pacemakers, Left Branch Bundle Block, Right Branch Bundle Block, intra ventricular conduction defect, or any other form of conduction defect disease, are often candidates for undergoing cardiac computed tomography (CT) imaging to assess cardiac chamber geometry and function to treat many medical conditions. Two factors that are taken into consideration in medical imaging are image quality and radiation exposure. To improve image quality, cardiac imaging in most modalities, such as CT, magnetic resonance (MR), nuclear, and others, requires gating of the images to a particular phase of the cardiac cycle. The timing of gating of the cardiac image is usually calculated with respect to the detected R-wave from an electrocardiograph signal from the patient. The duration of a representative cardiac cycle is typically based on the average or median of three or more previous R-to-R intervals, and the phase of the cardiac cycle of interest is typically based on a percent of the representative cardiac cycle duration. However, appreciable variation of paced heart rhythms and abnormal EKG complexes may degrade the image quality and interfere with the means to reduce the radiation dosage using electrocardiogram (ECG, or alternatively EKG) modulation for example.

The presence of pacer spikes and intrinsic beats in a paced EKG, particularly those that produce variable trigger delays, may lead to poor image quality (misregistration observed as a projection or abrupt offset of an otherwise smooth edge or surface of the reconstructed cardiac image) due to the reconstruction of cardiac images from incorrect phases of the cardiac cycle. As used herein, the term pacer refers to a pacemaker, an ICD (implanted cardiac defribillator), or any other device used at least partially for pacing the heart. As used herein, trigger delays refers to a delayed trigger (positive delay) or an early trigger (negative delay). Misregistration may occur in a variety of imaging modalities, including helical CT (Computed Tomography), electron beam CT, MR (Magnetic Resonance), Nuclear/PET (positron emission tomography), and other modalities that use gating for reconstructing images at selected phases of the cardiac cycle. Trigger delays as small as about 15 milliseconds have been found to result in poor image quality in some instances. When substantial trigger delays occur due to pacing, images from incorrect phases of the cardiac cycle are combined with images from correct phases, resulting in misregistration. As a result, R-wave delay, relative to the duration of the representative cardiac cycle, is a contributing factor to misregistration and poor image quality in patients having abnormal heartbeats. As used herein, the term abnormal heartbeat includes paced heart rhythm and abnormal EKG.

Accordingly, there is a need in the art for an apparatus and method for cardiac imaging of a patient with a pace-maker and/or a defibrillator.

SUMMARY OF INVENTION

Embodiments of the invention provide a method for acquiring cardiac information from a patient having a pacer for pacing a heart rhythm, an abnormal EKG, or an abnormal heartbeat. A signal injection device is placed proximate the pacer of the patient and a signal is injected across a skin barrier of the patient toward the pacer. In response to the signal being received at the pacer, the patient's heart is paced in a fixed asynchronous pacing mode, and cardiac information relating to the patient's fixed asynchronously paced heart is acquired.

Further embodiments of the invention provide a method for acquiring a cardiac image from a patient having a pacer for pacing a heart rhythm, an abnormal EKG, or an abnormal heartbeat. A gated electrocardiogram signal having local maxima and minima values and trigger points is received, and the time between each trigger point and the associated local maxima or minima is determined for a period of time. In response to the trigger point occurring at the associated local maxima or minima, a zero time differential is calculated for a corrected trigger for gating. In response to the trigger point occurring prior to the associated local maxima or minima, a time delay is calculated for the corrected trigger. In response to the trigger point occurring after the associated local maxima or minima, a time advancement is calculated for the corrected trigger. The corrected trigger is sent to a cardiac image acquisition device for gating, wherein the gating is substantially synchronized with the local maxima or minima of the gated electrocardiogram signal. A signal injection device is placed proximate the pacer of the patient and a signal is injected across a skin barrier of the patient toward the pacer. In response to the signal being received at the pacer, the patient's heart is paced in a fixed asynchronous pacing mode, and a cardiac image of the patient's fixed asynchronously paced heart is acquired.

Yet further embodiments of the invention provide an apparatus having electrocardiogram-gated acquisition and cardiac imaging capabilities for use with a patient having a pacer. The apparatus has an electrocardiograph, a cardiac scanner in signal communication with the electrocardiograph, an interface board in signal communication intermediate the electrocardiograph and the cardiac scanner, and a storage medium, readable by a processing circuit, for storing instructions for execution by the processing circuit. The stored instructions enable the processing circuit to: receive from the electrocardiograph a gated electrocardiogram signal having local maxima and minima values and trigger points; determine for a period of time the time between each trigger point and the local maxima or minima associated therewith; in response to the trigger point occurring at the associated local maxima or minima, calculate a zero time differential for a corrected trigger for gating; in response to the trigger point occurring prior to the associated local maxima or minima, calculate a time delay for the corrected trigger; in response to the trigger point occurring after the associated local maxima or minima, calculate a time advancement for the corrected trigger; and, send the corrected trigger to a cardiac image acquisition device for gating, wherein the gating is substantially synchronized with the local maxima or minima of the electrocardiogram signal. The patient is responsive to a signal injection device being placed proximate the pacer of the patient, where the signal injection device is adapted to inject a signal across a skin barrier of the patient toward the pacer. In response to the signal being received at the pacer, the patient's heart is paced in a fixed asynchronous pacing mode, and a cardiac image of the patient's fixed asynchronously paced heart is acquired at the cardiac image acquisition device.

BRIEF DESCRIPTION OF DRAWINGS

Referring to the exemplary drawings wherein like elements are numbered alike in the accompanying Figures:

FIG. 5 depicts an exemplary pacer for use with embodiments of the invention.

DETAILED DESCRIPTION

Embodiments of the invention provide a method and apparatus for acquiring a cardiac image from a patient having an abnormal heartbeat. While exemplary embodiments described herein depict an electrocardiogram of a patient having a pacemaker as the cause of the abnormal heartbeat, it will be appreciated that embodiments of the disclosed invention may also be applicable to other causes of abnormal heartbeats, such as Left Branch Bundle Block, Right Branch Bundle Block, intra ventricular conduction defect, other forms of conduction defects and irregular and abnormal heart beat as seen in patients with atrial fibrillation, for example.

Figure 1:
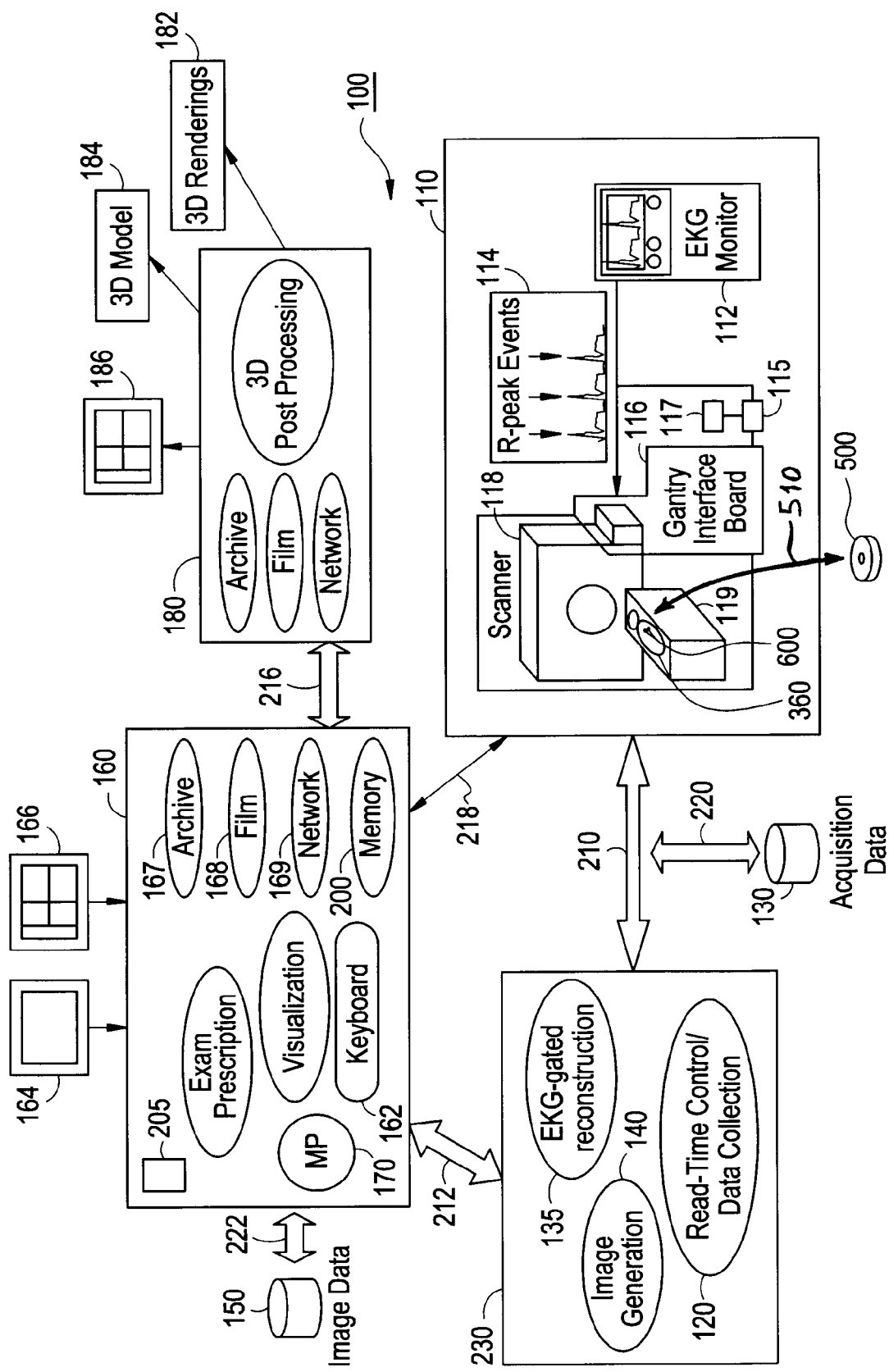
FIG. 1 depicts an exemplary system for implementing an embodiment of the invention.

FIG. 1 depicts an exemplary embodiment of an imaging system 100 for use in medical intervention procedure planning, such as biventricular pacing planning, atrial fibrillation ablation or other diagnostic and therapeutic interventions where CT imaging may be needed to get the appropriate information, for example. The imaging system 100 includes: a medical scanner system 110 for generating cardiac image data, such as, for example, image data of the right atrium and the coronary sinus, a data acquisition system 120 for acquiring the cardiac image data from medical scanner system 110, an acquisition database 130 for storing the cardiac image data from data acquisition system 120, an image generation system 140 for generating a viewable image from the cardiac image data stored in acquisition database 130, an image database 150 for storing the viewable image from image generation system 140, an operator interface system 160 for managing the medical scanner system 110 and the cardiac image data and viewable image in databases 130, 150, and a post-processing system 180 for analyzing and displaying the viewable image in database 150 and being responsive to operator interface system 160. Scanned data that is capable of being converted into a viewable image is referred to herein as image data.

System communication links 210, 212, 216, 218 and database communication links 220, 222 provide a means for signal communication amongst and between systems 110, 120, 140, 160, 180 and databases 130, 150. Communication links 210-222 may be hardwired or wireless. Operator interface system 160 may be a standalone input/output terminal or a computer including instructions in a variety of computer languages for use on a variety of computer platforms suitable for performing an embodiment of the invention disclosed herein.

Operator interface system 160 includes a processor 170, such as, for example, a microprocessor (MP), for managing the medical scanner system 110, for managing the data acquisition and image generation systems 120, 140, for processing and managing the information in acquisition and image databases 130, 150, and for managing the post-processing at post-processing system 180. Operator interface system 160 also includes: a memory 200 that contains specific instructions relating to electrocardiogram-gated acquisition and cardiac imaging, user input means, such as, for example, a keyboard 162, and user output means, such as, for example, displays 164, 166. Display 164 may be adapted for exam prescription, and display 166 may be adapted for visualization. Alternatively, displays 164 and 166 may be integrated into one display. In an alternative embodiment, scanner system 110 may include a memory 117 that contains specific instructions relating to electrocardiogram-gated acquisition and cardiac imaging, and a processor 115 for executing the instructions at memory 117. Memory 117 may be any memory suitable for storing executable instructions, including a CD-ROM.

Medical scanner system 110 includes an electrocardiogram (EKG) monitor (alternatively electrocardiograph) 112 that outputs electrocardiogram signals 114, such as R-peak events with gating (irregular EKG-gated signals are discussed later in reference to FIG. 2), through an interface board 116 into a scanner 118. A patient table 119 provides a stable surface for a patient (not shown) undergoing data acquisition via electrocardiograph 112 and scanner 118. Alternatively, interface board 116 may be used to couple EKG monitor 112 to scanner 118, and memory 117 and processor 115 may be integrated therewith. An example of an interface board 116 is a Gantry interface board. In an exemplary embodiment, scanner 118 is a cardiac computed tomography (CT) system with support for cardiac imaging, however, the illustrated scanner 118 is for exemplary purposes only; other imaging systems may also be used. Examples of other imaging systems include, but are not limited to, X-ray systems (including both conventional and digital or digitized imaging systems), magnetic resonance (MR) systems, positron emission tomography (PET) systems, ultrasound systems, nuclear medicine systems, and 3D fluoroscopy systems. Medical scanner system 110 also includes EKG gated acquisition or image reconstruction 135 capabilities for imaging of the heart. Medical scanner system 110 further includes circuitry for acquiring image data and for transforming the data into a useable form that is then processed to create a reconstructed image of features of interest within the patient. The image data acquisition and processing circuitry is often referred to as a "scanner", regardless of the type of imaging system employed, since some sort of physical or electronic scanning often occurs in the imaging process. The particular components of the system and related circuitry differ greatly between imaging systems due to the different physics and data processing requirements of the different systems. However, it will be appreciated that the present invention may be applied regardless of the selection of a particular imaging system.

In an embodiment, data is output from electrocardiograph 112 in the form of electrocardiogram signals 114, which may include gating triggers discussed later in reference to FIG. 2. The data is then analyzed at processor 115, executing instructions from memory 117 in accordance with embodiments of the invention depicted in the flowchart of FIG. 3 discussed later, to provide a corrected trigger for better synchronization of the gating of scanner 118 in the presence of an abnormal heartbeat. Data from scanner system 110 is output to subsystem 230 that itself may include software in data acquisition system 120 to control the data acquisition at scanner 118, and software in image generation system 140 to control image generation from the image data. Operational control may be provided by operator interface system 160 or within subsystem 230 via communication link 212. Data that is output from the scanner system 110, including imaging data and electrocardiogram signals 114, may be stored in acquisition database 130. Data acquisition in system 120 may be performed according to one or more acquisition protocols that are optimized for imaging the heart, and specifically for imaging the right ventricle for pacemaker lead placement. Image generation in system 140 may be performed using one or more optimized 3D protocols for automated cardiac imaging of a pacemaker patient showing lead placement.

In an embodiment, image data from image generation system 140 is communicated via link 212 to operator interface system 160. The image data used by software at operator interface system 160 for exam prescription and visualization is stored in image database 150. The image data may be archived 167, put on film 168, or sent over a network 169, to post-processing system 180 for analysis and review, including 3D post-processing. Reconstructed views may be saved to a 3D rendering file 182, and a geometric model of these structures and substructures may be saved to a 3D model file 184. Files 182 and 184 may be saved at image database 150 and may be viewed by the operator of operator interface system 160 during either the medical planning of an intervention procedure or during an interventional procedure itself, which may be viewed in combination with a projection image during a 3D-fluoroscopy procedure, alternatively referred to as an interventional image. The operator may view the 3D rendering and model 182, 184 on a display 186, which may be integrated with displays 164 and 166. In another embodiment, operator interface system 160 may contain the functions of the post-processor system 180.

Figure 2:
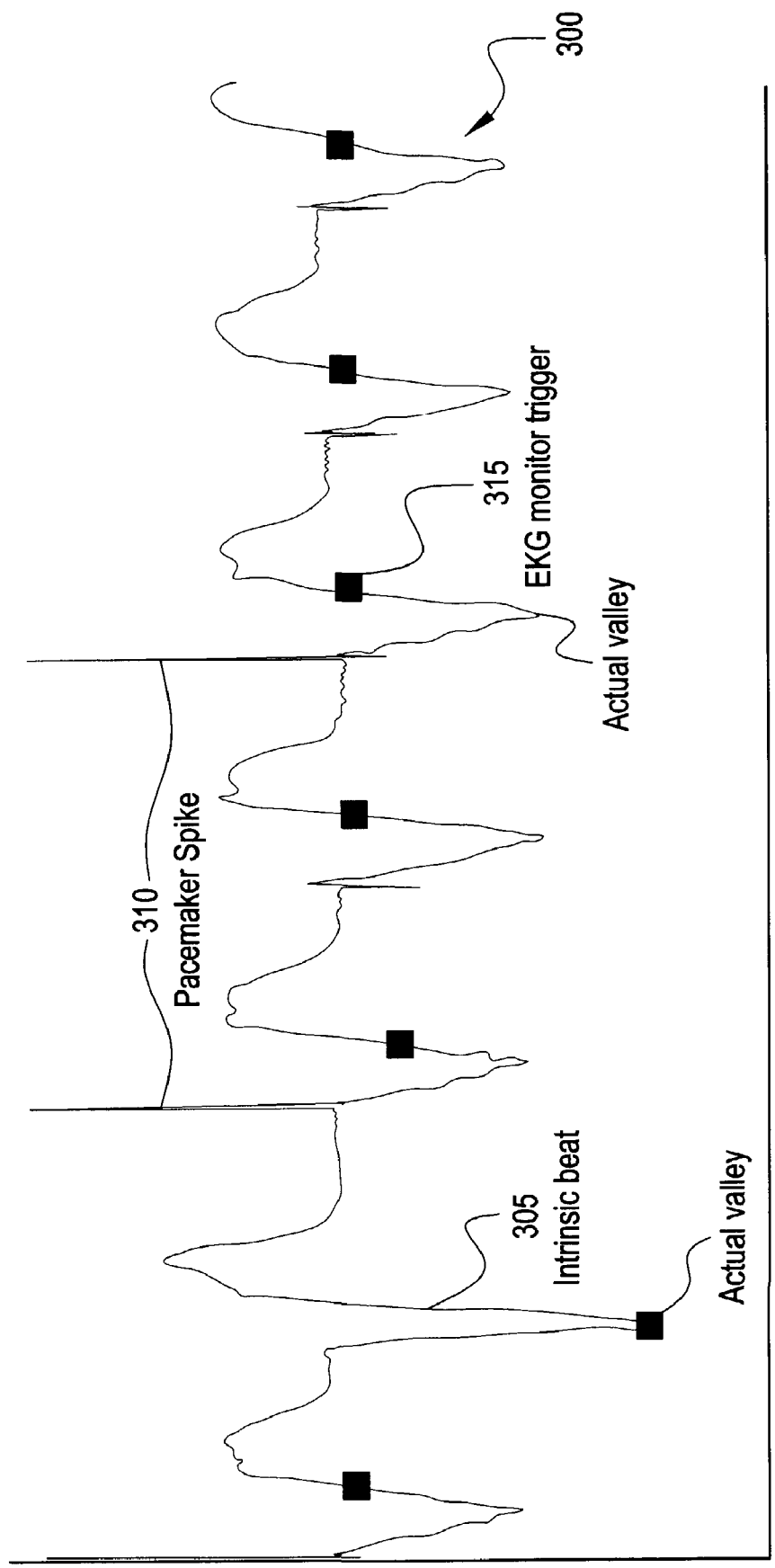
FIG. 2 depicts an exemplary gated-electrocardiogram of an abnormal heartbeat for use with an embodiment of the invention.

Referring now to FIG. 2, a gated-EKG signal 300 of a pacemaker patient with one intrinsic heartbeat 305 and two pacemaker spikes 310, as received and displayed at cardiograph 112, is depicted. Signal 300 is referred to as a QS (absent from initial or R wave deflection), as determined by the direction of the electrophysiological signal detected at the lead. Also absent is a distinct R-wave, due to pacing in the right ventricle. Accordingly, image acquisition gating with respect to triggering on the upstroke wave or peaks instead of a valley would result in poor synchronization for imaging. Also depicted in FIG. 2 are several EKG monitor trigger points 315 (depicted as solid boxes), which are normally used for gating scanner 118. These trigger points which are depicted as solid boxes at location 315 and are currently on the upstroke of the valley because of the presence of pacemaker spikes. At location 305, where an intrinsic beat occurs, the trigger point is at the valley, which is the correct location. In an embodiment, a process corrects the "paced heart rhythms" and abnormal EKGs so that the interpretation of the trigger will be at the correct valley or peak without delay. As can be seen, EKG monitor trigger points 315 are not substantially synchronized with a particular point on the waveform of gated-EKG signal 300. To provide a corrected trigger for the abnormal heartbeat depicted in FIG. 2, an embodiment of the invention, as illustrated in flowchart format in FIG. 3, is employed.

Figure 3:
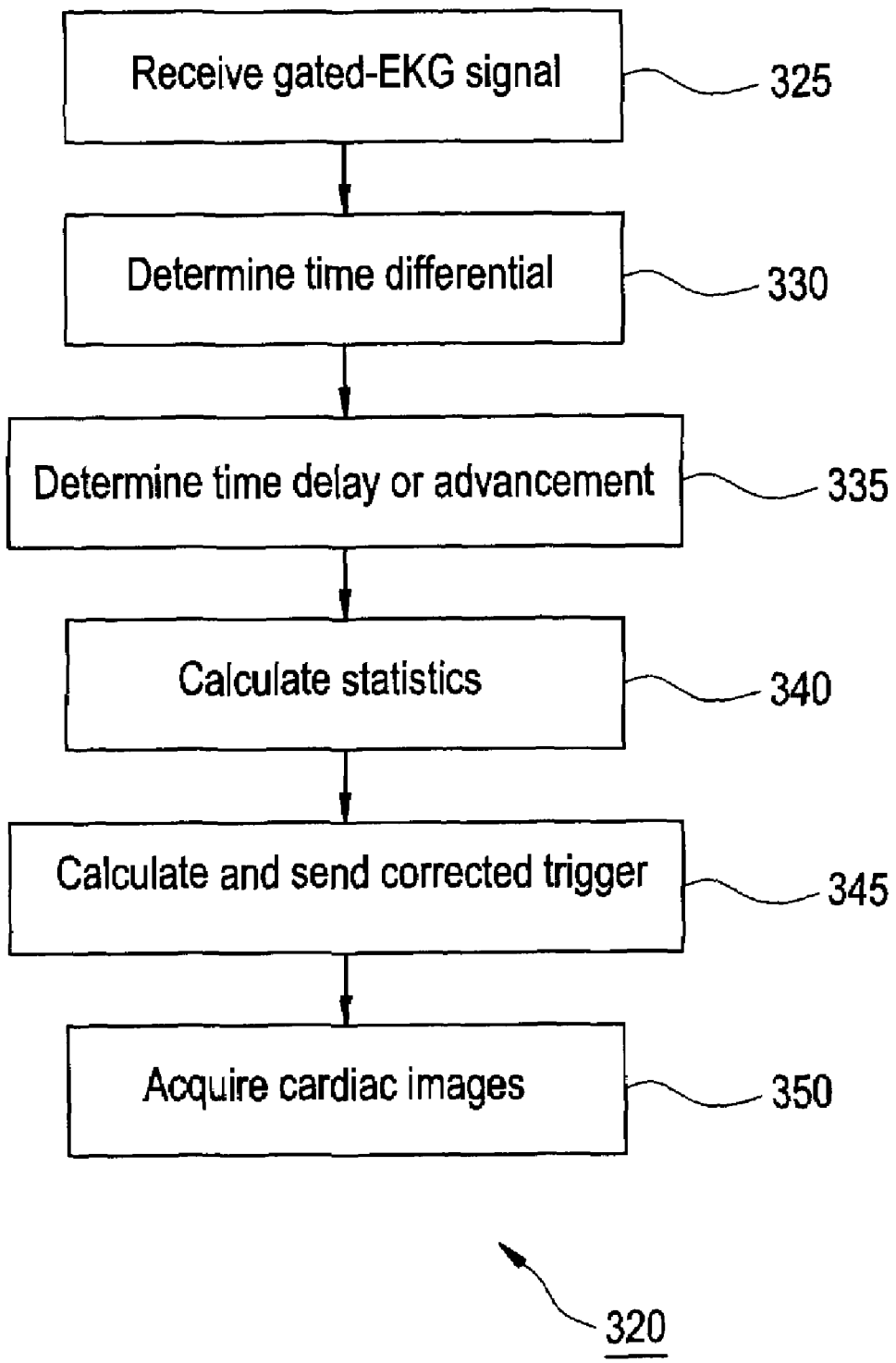
FIG. 3 depicts an exemplary method for implementing an embodiment of the invention.

Referring now to FIG. 3, a method 320 for acquiring a cardiac image from a patient having an abnormal heartbeat is depicted. At block 325, a gated-EKG signal 300 is received at processor 115, which may be integral with scanner 118 for rapid processing and image data acquisition. Gated-EKG signal 300 may be recorded prior to or concurrent with the imaging at scanner 118. However, if gated-EKG signal 300 is statistically unstable, as discussed later, then gated-EKG signal 300 may be recorded concurrent with the imaging at scanner 118. Gated-EKG signal 300 includes local maxima and minima values (such as S and T in FIG. 2 for example) and trigger points 315. At block 330, a delay processing algorithm determines for a period of time, such as about 20 seconds for example but other times may be used as appropriate, the time between each trigger point and the local maxima or minima associated therewith. If the current triggering location coincides with the local maxima or minima, then no triggering adjustment or delay calculation is necessary. However, if the current triggering location does not coincide with the local maxima or minima, then the data of gated-EKG signal 300 is walked through and compared sample by sample, with each value being stored at memory 117 until a local maxima or minima potential is found and the time differential determined based on the EKG sampling rate and the time difference between the trigger point 315 and the associated local maxima or minima. At block 335, if the EKG trigger 315 occurs prior to the associated local maxima or minima, then a corrected trigger for imaging is calculated as a time delay, and if the EKG trigger 315 occurs after the associated local maxima or minima, then a corrected trigger for imaging is calculated as a time advancement. At block 340 and for the period of time discussed earlier, statistical or probability calculations, such as average, range, standard deviation, or Bayesian probabilities, are made for the time differentials determined in block 330. At block 345, and in response to the range and standard deviation for the time differential being equal to or less than defined limits, a corrected trigger based on the average time differential is calculated and sent to scanner 118 for gating. However, in response to at least one of the range and the standard deviation for the time differential being greater than a defined limit, a corrected trigger for the present heartbeat based on the time differential of the prior heartbeat is calculated and sent to scanner 118 for gating. In an embodiment, the defined limit for the time differential range is about 10 milliseconds, and the defined limit for the time differential standard deviation is about 3 milliseconds. Other time values may be used as appropriate. By providing a corrected trigger to scanner 118, image acquisition gating may be substantially synchronized with the local maxima or minima of the irregular electrocardiogram signal. As used herein, the term substantially synchronized refers to the degree of synchronization being within defined statistical limits, as discussed previously. In an embodiment, the corrected trigger signals are first sent to data acquisition system 120, which processes the signals based on heart rate, real time, retrospective or prospective gating, and helical or cine scanning, and then provides a control signal for data acquisition at scanner 118. At block 350, cardiac images of the abnormal heartbeat are acquired at scanner 118, and in an embodiment, the images are acquired after the period of time, discussed earlier in reference to block 330, for determining the time between each trigger point and the associated local maxima or minima. By compiling time differential data for each heart beat and processing the data concurrently with the output signals for scanning decisions, method 320 enables image acquisition gating to be processed using a corrected trigger on a beat by beat basis, or on a statistical average time differential basis, thereby enhancing the quality of the cardiac image for an abnormal heartbeat.

In an alternative embodiment, the time differential statistics or probabilities calculated in block 340 may be calculated in real time on a sliding window basis, of about 20 seconds for example, so that the time differential and related statistics or probabilities for the corrected trigger may be continually updated, thereby providing an intelligent design capable of learning and anticipating future delays for providing high quality cardiac imaging of an abnormal heartbeat.

An embodiment of the invention may be provided in executable instruction form on a storage medium, such as memory 117 in the form of a CD-ROM for example, that is readable by a processing circuit, such as processor 115 for example, the processing circuit being in signal communication via application software with a graphical user interface at a computer, such as operator interface 160 for example, whereby a user may execute the embedded instructions for practicing the disclosed invention. The technical effect of the executable instructions is to enhance the quality of the cardiac image for an abnormal heartbeat on a system adapted for electrocardiogram-gated acquisition and cardiac imaging.

Separate from or in combination with imaging system 100 and method 320, a method for acquiring cardiac information, such as an EKG signal or cardiac images, from a patient having a pacer responsive to a signal injection device may also be implemented.

Figure 4:
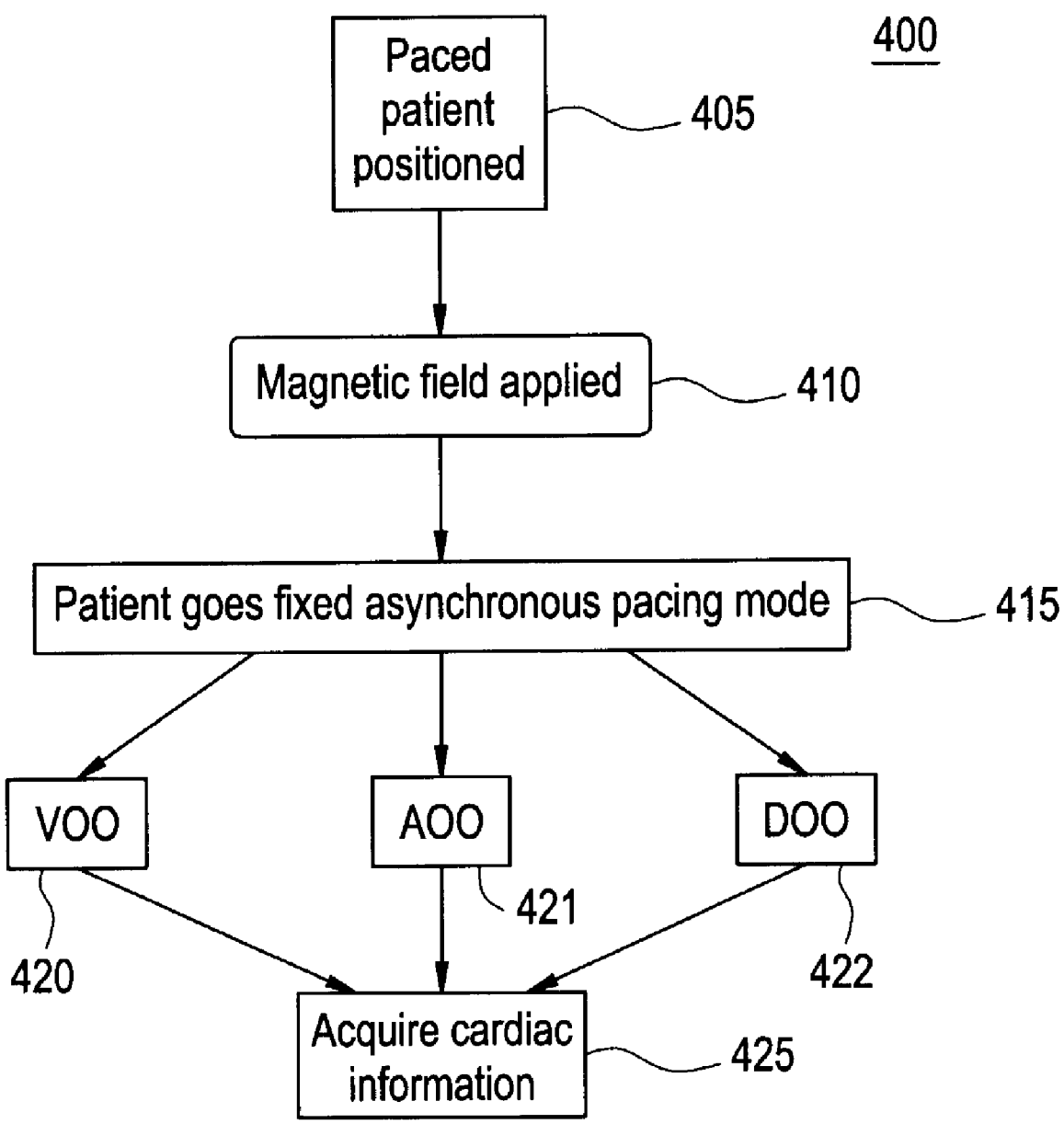
FIG. 4 depicts an exemplary method for implementing another embodiment of the invention.

Referring now to FIGS. 1, 4 and 5, a method 400 (see FIG. 4) for placing a paced patient 360 (see FIG. 1) in a fixed asynchronous pacing mode is depicted. At block 405, a paced or ICD patient 360 is positioned on table 119 in preparation for cardiac imaging. At block 410, a signal injection device 500 (see FIG. 1) is placed over a pacer 600 (see FIGS. 1 and 5) of patient 360, and a signal is injected across the skin barrier of patient 360 toward pacer 600. Signal injection device 500 may be adapted to produce a magnetic signal, a wireless signal, an x-ray signal, a microwave signal, an infrared signal, or any combination of signals including at least one of the foregoing. The signal generated by signal injection device 500 may be a fixed signal or a pulsed signal. In an embodiment, signal injection device 500 is a magnetic signal injection device that includes a fixed magnet, an electromagnet, or a combination of both, and is capable of producing a magnetic signal having a signal strength at pacer 600 of equal to or greater than about 90 Gauss when placed at a distance equal to or less than about 2 inches from pacer 600. In an embodiment, the outside diameter of magnetic signal injection device 500, which is depicted in FIG. 1 as a donut-shaped device having a central hole therethrough, is equal to or greater than an outside diameter of pacer 600 (see FIG. 5 for a more detailed view of pacer 600). While magnetic signal injection device 500 and pacer 600 are depicted having circular geometry's that define dominant outside dimensions by respective outside diameters, it will be appreciated that other geometry's may be employed where a dominant outside dimension of magnetic signal injection device 500 is equal to or greater than a dominant outside dimension of pacer 600.

Referring briefly to FIG. 5, an exemplary pacer 600 in the form of a pacemaker is depicted have a circular case 605 housing a pulse generator 610, the case 605 having an outside diameter that is a dominant dimension with respect to pacer 600 overall, a header 615 housing a control and power supply assembly 620, and leads 625 with terminals 630 at each respective end. Included on assembly 620 is a switch 635 that is responsive to a signal, such as a magnetic field from magnetic signal injection device 500, for switching pacer 600 into and out of a fixed asynchronous pacing mode. Pacer 600 is typically located beneath the skin of patient 360 in a region near the patient's left shoulder.

Referring now back to FIG. 4, pacer 600 is responsive to the signal received from magnetic signal injection device 500 in such a manner that activates switch 635 to place pacer 600, and therefore patient 360, in a fixed asynchronous pacing mode, as depicted at block 415 in method 400, independent of the patient's own natural heart rhythm. The heart mode that the patient was in prior to magnetic signal injection, ventricular asynchronous mode (VOO), atrial asynchronous mode (AOO), or dual-chambered asynchronous mode (DOO), will dictate which fixed asynchronous pacing mode the patient will be in subsequent to magnetic signal injection, as depicted at blocks 420, 421, 422, where the before and after modes are the same.

A VOO timing cycle consists of defined rates, such as 80 beats-per-minute for example, where pacer 600 delivers a ventricular pacing artifact at this defined rate regardless of intrinsic heart activities. In a VOO timing cycle, the intervals between paced complexes remain stable. AOO asynchronous pacing behaves similar to VOO, but the artifacts occur in the atrium instead of the ventricle. DOO asynchronous pacing occurs in an AV (atrium-then-ventricle) sequence. These asynchronous pacing modes, which, as discussed previously, may be implemented via magnetic signal injection, are insensitive to many if not all intrinsic events.

At block 425, cardiac information is acquired via imaging system 100 while patient 360 is in a fixed asynchronous pacing mode. In an embodiment, the cardiac information acquired may be an EKG signal at EKG monitor 112, or a series of cardiac image data taken at scanner 118. Where EKG monitor 112 is employed, the mode of the patient 360 and/or pacer 600 before and after signal injection will be displayable.

When magnetic signal injection device 500 is used in combination with imaging system 100, as discussed previously, the patient's abnormal heartbeat may first be corrected and then placed in a fixed asynchronous pacing mode for further improving cardiac image quality.

While embodiments of the invention have been described with reference to improving cardiac imaging for subsequent medical procedures that benefit therefrom, it will be appreciated that the teachings herein may also be applied to emergency medical devices that are capable of switching a patient's pacemaker from a first mode to a second mode, where the P-R interval of the patient's heart may be temporarily lengthened to improve blood flow under strenuous conditions.

Some embodiments of the invention have some of the following advantages: improved quality of the cardiac image; automated signal correction for abnormal EKG patients where triggering on their QRS complex may cause difficulty; reduced exposure to ionizing radiation as a result of improved image acquisition gating and heart rhythm control, and therefore reduced time requirement for successful imaging; automated recalculation of signal statistics for intelligent real time adjustment of the time differential for the corrected trigger in combination with heart rhythm control; improved control of a patient's heart rhythm to further improve cardiac images from gating across multiple modalities; a value added step for radiologists that brings closer the field of electrophysiology to radiology; and, the elimination of the appearance of mixed intrinsic and paced rhythms that are a substantial hindrance to cardiac gating.

While the invention has been described with reference to exemplary embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best or only mode contemplated for carrying out this invention, but that the invention will include all embodiments falling within the scope of the appended claims. Moreover, the use of the terms first, second, etc. do not denote any order or importance, but rather the terms first, second, etc. are used to distinguish one element from another. Furthermore, the use of the terms a, an, etc. do not denote a limitation of quantity, but rather denote the presence of at least one of the referenced item.

The invention claimed is:

1. A method for acquiring a cardiac image from a patient having a pacer for pacing a heart rhythm, an abnormal EKG, or an abnormal heartbeat, the method comprising:
   receiving a gated electrocardiogram signal having local maxima and minima values and trigger points;
   determining for a period of time the time between each trigger point and the local maxima or minima associated therewith;
   in response to the trigger point occurring at the associated local maxima or minima, calculating a zero time differential for a corrected trigger for gating;
   in response to the trigger point occurring prior to the associated local maxima or minima, calculating a time delay for the corrected trigger;
   in response to the trigger point occurring after the associated local maxima or minima, calculating a time advancement for the corrected trigger;
   sending the corrected trigger to a cardiac image acquisition device for gating, wherein the gating is substantially synchronized with the local maxima or minima of the gated electrocardiogram signal;
   placing a signal injection device proximate the pacer of the patient and injecting a signal across a skin barrier of the patient toward the pacer;
   in response to the signal received at the pacer, pacing the patient's heart in a fixed asynchronous pacing mode; and
   acquiring a cardiac image of the patient's fixed asynchronously paced heart.

2. The method of claim 1, wherein the signal injection device is a magnetic signal injection device comprising at least one of a fixed magnet and an electromagnet.

3. The method of claim 2, further comprising:
   in response to the magnetic signal received at the pacer, activating a switch at the pacer for pacing the patient in a fixed asynchronous pacing mode.

4. The method of claim 2, wherein the magnetic signal injection device is adapted to produce a magnetic signal having a signal strength at the pacer equal to or greater than about 90 Gauss when placed at a distance equal to or less than about 2 inches from the pacer.

5. The method of claim 2, wherein the magnetic signal injection device has an outside dimension equal to or greater than an outside dimension of the pacer.

6. The method of claim 1, wherein the fixed asynchronous pacing mode includes a ventricular, an atrial, or a dual chamber asynchronous pacing mode.

7. A method for acquiring cardiac information from a patient having a pacer for pacing a heart rhythm, an abnormal EKG, or an abnormal heartbeat, the method performed using an apparatus having electrocardiogram-gated acquisition and cardiac imaging capabilities for use with a patient having a pacer, the apparatus comprising an electrocardiograph, a cardiac scanner in signal communication with the electrocardiograph, an interface board in signal communication intermediate the electrocardiograph and the cardiac scanner, and a storage medium, readable by a processing circuit, storing instructions for execution by the processing circuit for performing aspects of the method, the method comprising:
   receiving a gated electrocardiogram signal having local maxima and minima values and trigger points;
   determining for a period of time the time between each trigger point and the local maxima or minima associated therewith;
   in response to the trigger point occurring at the associated local maxima or minima, calculating a zero time differential for a corrected trigger for gating;
   in response to the trigger point occurring prior to the associated local maxima or minima, calculating a time delay for the corrected trigger;
   in response to the trigger point occurring after the associated local maxima or minima, calculating a time advancement for the corrected trigger;
   sending the corrected trigger to a cardiac image acquisition device for gating, wherein the gating is substantially synchronized with the local maxima or minima of the gated electrocardiogram signal;
   placing a signal injection device proximate the pacer of the patient and injecting a signal across a skin barrier of the patient toward the pacer;
   in response to the signal received at the pacer, pacing the patient's heart in a fixed asynchronous pacing mode; and
   acquiring cardiac information relating to the patient's fixed asynchronously paced heart; and
   acquiring a cardiac image of the patient's fixed asynchronously paced heart.

* * * * *